(12) United States Patent
Choi et al.

(10) Patent No.: US 9,771,393 B2
(45) Date of Patent: Sep. 26, 2017

(54) BIOACTIVE PEPTIDES HAVING INSECTICIDE ACTIVITY

(71) Applicant: The United States of America, as represented by the Secretary of Agriculture, Washington, DC (US)

(72) Inventors: Man-Yeon Choi, Gainesville, FL (US); Robert K. Vander Meer, Newberry, FL (US)

(73) Assignee: The United States of America, as represented by The Secretary of Agriculture, Washington, DC (US)

(*) Notice: Subject to any disclaimer, the term of this patent is extended or adjusted under 35 U.S.C. 154(b) by 0 days.

(21) Appl. No.: 15/067,522

(22) Filed: Mar. 11, 2016

(65) Prior Publication Data

US 2016/0262388 A1  Sep. 15, 2016

Related U.S. Application Data

(60) Provisional application No. 62/131,342, filed on Mar. 11, 2015.

(51) Int. Cl.
*C07K 7/06* (2006.01)
*A01N 37/46* (2006.01)

(52) U.S. Cl.
CPC ............... *C07K 7/06* (2013.01); *A01N 37/46* (2013.01); *G01N 2333/43552* (2013.01); *G01N 2333/726* (2013.01); *G01N 2430/10* (2013.01); *G01N 2500/10* (2013.01)

(58) Field of Classification Search
CPC ............ A01N 37/46; C07K 7/06; G01N 2333/43552; G01N 2333/726; G01N 2430/10; G01N 2500/10
USPC .......................... 530/327; 514/4.5, 21.5, 21.6
See application file for complete search history.

(56) References Cited

U.S. PATENT DOCUMENTS

2003/0166549 A1* 9/2003 Schughart ............... C07K 7/08
514/1.2

OTHER PUBLICATIONS

Bradley et al., "Limits of Cooperativity in a Structurally Modular Protein: Response of the Notch Ankyrin Domain to Analogous Alanine Substitutions in Each Repeat," J. Mol. Biol., 2002, 324: 373-386.*
Ngo et al., "Computational COplexity, Protein Structure Prediction, and the Levinthal Paradox," The Protein Folding Problem and Tertiary Structure Prediction, K. Merz Jr. and S. Le Grand, Ed., Birkhauser Boston, 1994, 491-495.*
Berendsen HJC, "A Glimpse of the Holy Grail?" Science, 1998, 282: 642-643.*
RudingerJ, "Characteristics of the amino acids are components of a peptide hormone sequence," Peptide Hormones, J.A. Parsons, Ed., 1976, 1-7.*
Schinzel et al., "The phosphate recognition site of *Escherichia coli* maltodextrin phosphorylase," FEBS, 1991, 286(1,2): 125-128.*
"Designing Custom peptides," from SIGMA Genosys, Accessed Dec. 16, 2004. pp. 1-2.*
Voet et Voet, "Biochemistry" Second Edition, John Wiley & Sons, Inc., 1995, pp. 235-.*

* cited by examiner

*Primary Examiner* — Julie Ha
(74) *Attorney, Agent, or Firm* — John D. Fado; Mark D. McNemar

(57) ABSTRACT

Disclosed are novel bioactive peptides derived as antagonists to a fire ant receptor for a pheromone biosynthesis-activating neuropeptide/pyrokinin (PBAN/pyrokinin) gene derived neuropeptide ligand. Also disclosed are methods of controlling fire ants with the bioactive peptides disclosed herein. Methodological approaches to screening peptide libraries for the presence of PBAN/pyrokinin ligands are also provided herein.

15 Claims, 6 Drawing Sheets

BIOACTIVE PEPTIDES HAVING INSECTICIDE ACTIVITY

CROSS-REFERENCE

The present application claims priority to U.S. Provisional Patent Application Ser. No. 62/131,342 filed Mar. 11, 2015, the content of which is expressly incorporated herein by reference.

FIELD OF THE INVENTION

This invention relates to novel bioactive peptides for controlling a *Solenopsis* spp. and method to control *Solenopsis* spp. with disclosed peptides.

BACKGROUND OF INVENTION

Insect pests cost the general public billions of dollars annually in losses. These losses include the expense of controlling insect pests as well as crop loss and property damage caused by the pests. Economically significant insect pests in United States include *Solenopsis* spp. For *Solenopsis invicta* specifically, the well-documented fire ant currently infests over 320 million acres in the United States and over $6 billion per year is spent for control, agricultural losses, medical costs, and damage repair (as reported in Lard, C. F., et al., 2006, "An economic impact of imported fire ants in the United States of America." Texas A&M University, College Station, Tex. Available online at fireantecon.tamu.edu). Control of *Solenopsis invicta* is generally achieved through traditional chemical pesticides and/or delayed acting pesticides delivered as baits.

Chemical pesticides are the primary tools used to combat insect pests. However, use of traditional chemical pesticides has disadvantages, including non-target effects on neutral or beneficial insects, as well as other animals. Chemical pesticide usage also can lead to chemical residue run-off into streams and seepage into water supplies resulting in ecosystem/environment damage. In addition, animals higher in the food chain are at risk when they consume pesticide contaminated crops or insects. The handling and application of chemical pesticides also presents exposure danger to the public and professionals, and could lead to accidental dispersal into unintended environmentally sensitive areas. In addition, prolonged chemical pesticide application may result in an insect population becoming resistance to a chemical pesticide. In order to control a traditionally chemical resistant-pest, new more potent chemical pesticides must be utilized, which in turn will lead to another resistance cycle. As such, there is a need in the art to control pest populations without the disadvantages of traditional chemical pesticides.

Genes associated with signal transduction of neurohormones represent potential pesticide targets. One neurohormone gene family is the pheromone-biosynthesis-activating neuropeptide receptor (PBAN-R) gene family. PBAN-R is expressed in target tissue(s) in developmental and adult stages. The PBAN-R activates a specific physiological function after binding to a pheromone biosynthesis activating neuropeptide/pyrokinin (PBAN/pyrokinin) peptide ligand. To date, over 250 PBAN/pyrokinin family peptide ligands have been identified. Research on the function(s) of these peptide ligand(s)/receptor(s) has largely focused on the regulation of sex pheromones (Raina et al., 1989), and a variety of other physiological functions depending on life stages and insect groups: examples of known functions are induction of cuticle melanization, regulation of egg or pupal diapause, control of hind gut muscle (Matsumoto et al., 1990; Suwan et al., 1994; Sun et al., 2003; Nachman et al., 1986). These multi-functional PBAN/pyrokinin peptides are good targets to screen specific antagonist(s) through specific receptor-based expression. All PBAN-Rs belong to a family of G-protein coupled-receptors (GPCRs) which are 7-transmembrane receptors containing an extracellular N-terminal and intracellular C-terminal end in the cell membrane. SEQ ID NO: 13 GSGEDLSYGDAYEVDEDDHPLFVPRL is the specific PBAN ligand amino acid sequence for *Solenopsis invicta*.

The PBAN/Pyrokinin gene is expressed in all fire ant developmental stages (J. of Insect Physiology, 2012, 58, 1159-1165), as well as the adults, suggesting functions for the peptide ligands and their associated GPCRs throughout the fire ant life cycle. In addition, prevention of PBAN-R gene expression led to negative phenotypic effects on immature and adult fire ants (See, e.g., U.S. Pat. No. 8,575,328). Given the importance of PBAN-R in essential developmental and adult fire ant stages, discovery of novel peptide ligands that strongly bind to PBAN-R could prevent normal functioning of PBAN-R and act as alternatives or additives to classical chemical pesticides. To that end, there is a need to develop methodology to make and discover peptide ligands of PBAN-R that are effective for insect-control.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF SUMMARY OF THE INVENTION

Disclosed herein is an insecticide composition for controlling an insect, the composition comprising an effective amount of peptide having SEQ ID NO: 1. In one embodiment of the invention, the insecticide composition for controlling insects, comprises an effective amount of peptide having SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. In another embodiment of the invention, the insecticide composition further compromises an insecticide carrier. In one particular embodiment, the carrier is saline. In another embodiment of the invention, SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10 is combined with one or more suitable carriers, diluents, adjuvants, preservatives, dispersants, solvents, or emulsifying agents.

Disclosed herein is a spray composition for controlling an insect, the spray comprises of: (a) an effective amount of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10 and (b) a propellant.

Disclosed herein is a bait composition for controlling an insect, the bait comprises of: (a) an effective amount of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10, (b) one or more food materials; and (c) optionally a phagostimulant.

Disclosed herein is an insecticide composition for controlling *Solenopsis* spp., the composition comprises of an effective amount of peptide having SEQ ID NO: 11 or SEQ ID NO: 12. In another embodiment of the invention, the insecticide composition further compromises an insecticide carrier. In one particular embodiment, the carrier is saline. In another embodiment of the invention, SEQ ID NO: 11 or SEQ ID NO: 12 is combined with one or more suitable carriers, diluents, adjuvants, preservatives, dispersants, solvents, or emulsifying agents.

Also disclosed is a method for controlling an insect spp., the method comprises of contacting an insect or its environment with a biologically effective amount of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12, wherein the mortality of said insect increases. In one embodiment of the invention the insect is *Solenopsis invicta*.

Disclosed herein is a method of selecting peptides having an affinity for a target G-protein coupled-receptor, by a phage display technique, comprising the steps of: incubating a phage library with target insect cells and isolating the phage fraction bound to said cells.

BRIEF DESCRIPTION OF THE DRAWINGS

The present invention together with the disclosed embodiments may best be understood from the following detailed description of the drawings, wherein.

BRIEF DESCRIPTION OF THE SEQUENCES

Figure 1:
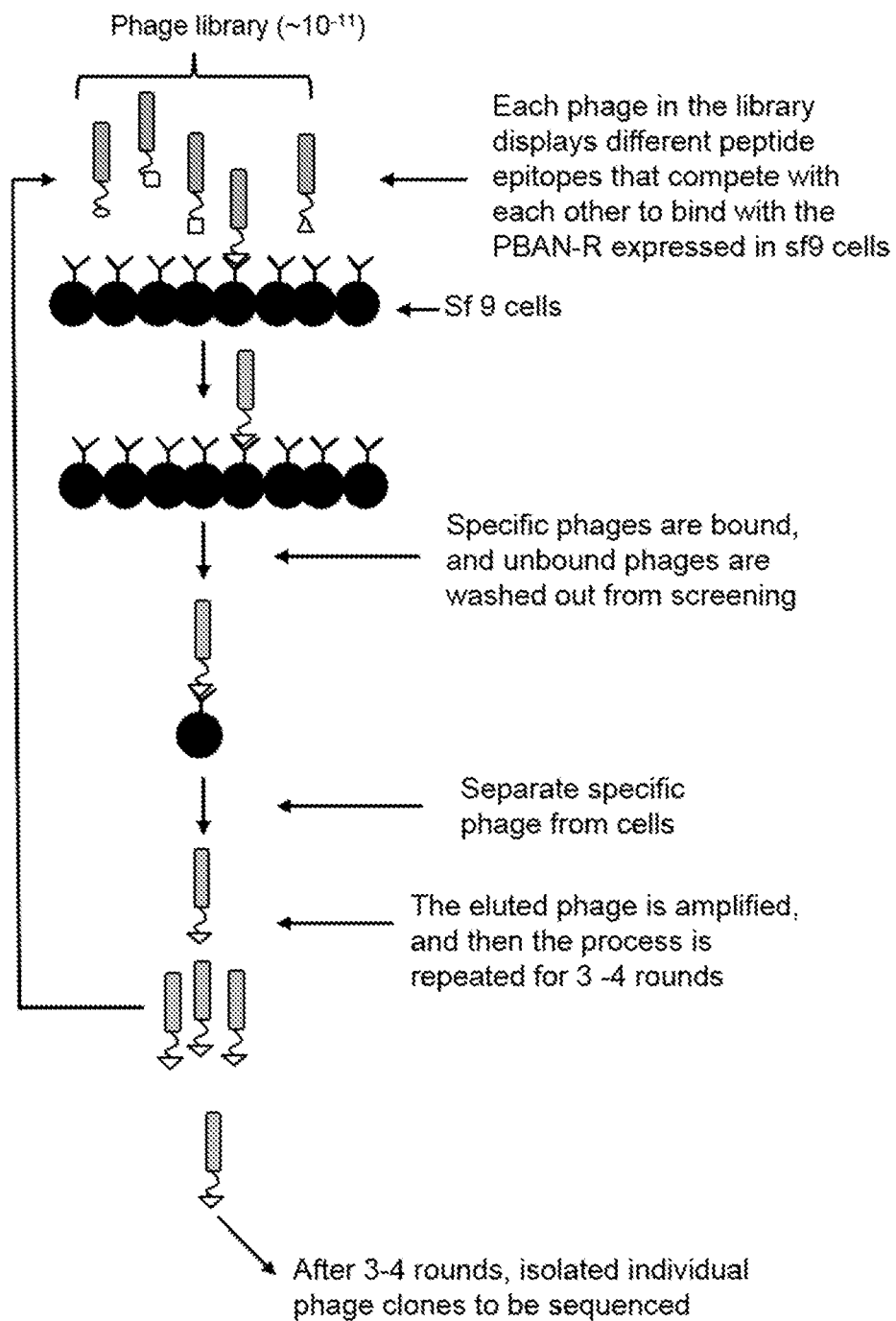
FIG. 1 is a depiction of a strategy to screen strongly binding peptides from isolated phage using insect cells expressing PBAN-R.

SEQ ID NO: 1: CXaaXaaXaaXaaSHFC is a peptide motif.

SEQ ID NO: 2: is CQKIGSHFC, a synthetically generated peptide.

SEQ ID NO: 3: is CLKIGSHFC, a synthetically generated peptide.

SEQ ID NO: 4: is CIQQGSHFC, a synthetically generated peptide.

SEQ ID NO: 5: is CERVGSHFC, a synthetically generated peptide.

SEQ ID NO: 6: is CVKLGSHFC, a synthetically generated peptide.

SEQ ID NO: 7: is CIVQGSHFC, a synthetically generated peptide.

SEQ ID NO: 8: is CQSINGHFC, a synthetically generated peptide

SEQ ID NO: 9: is CVKQGTHFC, a synthetically generated peptide.

SEQ ID NO: 10: is CIVQGSHFC, a synthetically generated peptide.

SEQ ID NO: 11: is CMARYMSAC, a synthetically generated peptide.

SEQ ID NO: 12: is CRGATPMSC, a synthetically generated peptide.

SEQ ID NO: 13: is GSGEDLSYGDAYEVDEDDH-PLFVPRL is PBAN amino acid sequence for *Solenopsis invicta*.

SEQ ID NO: 14: is CGSHFC, a synthetically generated peptide.

DETAILED DESCRIPTION OF THE INVENTION

Disclosed here are specific bioactive peptides that block the binding of PBAN receptor to PBAN as a means of interfering with critical functions of the PBAN receptor/ligand system, a novel method to develop biologically-based control for pest management is disclosed.

As used in the specification and claims, the singular form "a", "an", and "the" include plural references unless the context clearly dictates otherwise. For example, the term "a cell" includes a plurality of cells, including mixtures thereof.

The terms "isolated", "purified", or "biologically pure" as used herein, refer to material that is substantially or essentially free from components that normally accompany the referenced material in its native state.

The term "pheromone-biosynthesis-activating neuropeptide receptor" refers to a G-Protein coupled receptor, also known as a seven-transmembrane domain receptor, whose activating ligand(s) is derived from the 3 to 5 peptides produced by the PBAN/pyrokinin gene, specifically the PBAN peptide. The receptor is also referred to as "PBAN-R".

In the following description, the nomenclature used to define the proteins and peptides is that specified by Schroder and Lubke ["The Peptides" Academic Press (1965)] wherein, in accordance with conventional representation, the N-terminal appears to the left and the C-terminal to the right. Where the amino acid residue has isomeric forms, it is the L-form of the amino acid that is represented herein unless otherwise expressly indicated.

"Screening" refers to a technique used to select a specific peptide(s) expressed from a phage display library (containing >10$^9$ different peptides). Typically, peptides binds to a specific GPCR that is immobilized to a solid surface or coupled to a carrier protein prior to coating a solid surface such as microplate. A suspension containing the library of mobile phage peptides is swirled over the surface of the immobilized GPCR. Unbound phages are removed by washing. Phages bound to the immobilized GPCR that are acting as ligands and can then be removed.

"Phage display" is a method of using bacteriophages to express coat proteins or peptides for testing, particularly newly generated peptides (5-7 amino acids) thereof. A gene encoding a protein/peptide is cloned and inserted into a phage genome or genetic material in such a way that the protein/peptide is displayed (=expressed) on the surface of the phage, which is a recombinant phage. Effective phages can be selected by how tightly (affinity) the proteins or peptides are bound to the receptor expressed in cells. The non-bound phages can be removed by washing the cells expressing the receptor. The bound proteins/peptides produced by phages can then be isolated from the receptor and since they are still part of the phage, they can be grown in enough quantity to identify the gene sequence, and hence the protein sequence. This allows further manipulation of phages that bind to the target receptor(s).

"Phage display library" refers to a collection of random sequences of nucleic acids that have been inserted into phage vector and that code for vast numbers of different peptides thereof. The library can contain a few or a large number of random combinations of nucleic acid sequences, varying from about ten to several billion combinations of nucleotide sequences or more that code for a vast number ($\sim 10^{12}$) of random peptides.

The term "insect-control" with the peptides, as used herein, refers to the capacity to inhibit normal insect pupae or larvae development, make the insect infertile, inhibit pheromone production, induce mortality in the insect, or affect growth in any such manner that the pest insect population becomes economically unimportant. Results for controlling said insects include, but are not limited to, causing mortality to the insect, having the insect produce fewer offspring, are less fit or making the insect more susceptible to predator/parasite or pathogen attack.

An "effective amount" is an amount sufficient to effect desired beneficial or deleterious results. An effective amount can be administered in one or more administrations. In terms of treatment, an "effective amount" is that amount sufficient to make the target pest non-functional by causing an adverse effect on that pest, including (but not limited to) physiological damage to the pest; inhibition or modulation of pest growth; inhibition or modulation of pest reproduction; or death of the pest. In one embodiment of the invention, it is contemplated that a solution containing a bioactive peptide disclosed herein is ingested by an insect that controls said target insect.

The term "phagostimulant" refers to any substance that will entice the insect to ingest the selected bioactive peptide. Suitable phagostimulants include but are not limited to syrups, honey, aqueous solutions of sucrose, artificial sweeteners such as sucralose, saccharin, and other artificial sweeteners, amino acids, and other proteins. Additionally, the bait material containing the bioactive peptide disclosed herein would be incorporated in water soluble baits, oil-in water or oil/water emulsion baits, liquid type or gel type of baits.

The ready-to-use preparations of phagostimulants can be in the form of a wettable powder, flowable concentrate solution, water soluble granules, ultra-low volume formulation, and the like, which can be applied to the target insect habitat. Phagostimulants can be used in combination with peptides of the present invention to enhance or encourage uptake by target insects. In essence, the combination is an insect bait. Such baits can also include any other component desired by one of skill in the art, such as carriers, preservatives, odorants, insecticides and the like. Phagostimulants can include carbohydrates such as glucose, fructose, arabinose, sorbitol, maltose, glucose, lactose, or any other small sugar. In some embodiments, amino acids such as glycine, alanine, ornithine, phenylalanine, isoleucine and valine have all demonstrated phagostimulant properties for some insects. It will be obvious to a person skilled in the art that some carbohydrates and/or amino acids are likely to act as a deterrent. Thus, a bait, or other composition of the present invention can include phagostimulant(s) that attract a target insect and components that repel other animals (such as beneficial insects, pets and wildlife). Such variations are easily appreciated by any person skilled in the art.

The peptide sequences screened in this invention can be synthesized by any suitable method, such as exclusively solid-phase techniques, partial solid-phase techniques, fragment condensation, or classical solution addition. The amino acids of the compounds of the invention are typically joined to adjacent groups through amide linkages. For example, without being limited thereto, the peptide variants may be synthesized by methods well known to those skilled in the art of peptide synthesis, e.g., solution phase synthesis [see Finn and Hoffman, In "Proteins," Vol. 2, 3rd Ed., H. Neurath and R. L. Hill (eds.), Academic Press, New York, pp. 105-253 (1976)], or solid phase synthesis [see Barany and Merrifield, In "The Peptides," Vol. 2, E. Gross and J. Meienhofer (eds.), Academic Press, New York, pp. 3-284 (1979)], or stepwise solid phase synthesis as reported by Merrifield [J. Am. Chem. Soc. 85: 2149-2154 (1963)], the contents of each of which are incorporated herein by reference. However, the peptide fragments are preferably produced by recombinant DNA techniques which are particularly suitable for large-scale use.

Synthesis by the use of recombinant DNA techniques, for the purpose of this application, should be understood to include the suitable employment of structural genes coding for the sequence as specified hereinafter. The synthetic peptides may also be obtained by transforming a microorganism or plant using an expression vector including a promoter or operator, or both, together with such structural genes and causing such transformed microorganisms or plant to express the peptide.

Vectors used in practicing the present invention are selected to be operable as cloning vectors or expression vectors in the selected host cell. Numerous vectors are known to practitioners skilled in the art, and selection of an appropriate vector and host cell is a matter of choice. The vectors may, for example, be bacteriophage, plasmids, viruses, or hybrids thereof, such as those described in Maniatis et al. [Molecular Cloning: A Laboratory Manual, Cold Springs Harbor Laboratory, 1989] or Ausubel et al. [Current Protocols in Molecular Biology, John Wiley & Sons, Inc, 1995], the contents of each of which are herein incorporated by reference. Further, the vectors may be non-fusion vectors (i.e., those producing the peptides of the invention not fused to any heterologous polypeptide), or alternatively, fusion vectors (i.e., those producing the peptides fused to a vector encoded polypeptide). The fusion proteins would of course vary with the particular vector chosen.

All *S. invicta* samples were collected from monogyne (single functional queen) colonies collected from the Gainesville, Fla. USA area by excavation of nests or by establishing colonies directly from newly mated queens and maintained as described in W. A. Banks et al., "Techniques for collecting, rearing, and handling imported fire ants" (USDA, SEA, AATS-S-21, 9 p., 1981).

Screening for Peptide Antagonists Against PBAN-R

Phage display describes a technique in which a peptide or protein is fused with the coat protein of a bacteriophage, resulting in exposure of the fused protein on the surface of the virion. The peptides the phage displays are randomly generated at a specific number of amino acids (such as 7 amino acids in length in the preferred embodiment) creating a vast library of peptide sequences each of which are exposed on their unique phage surface. This allows the rapid identification of peptide ligands with a high affinity for a target cell-surface receptor, e.g. PBAN-R, by an in vitro selection process. The procedure for the screening of small peptides was initiated with a Step 1 screening round where a 10 uL phage library (~$10^{11}$ phage display peptides, New England Biolabs, Inc.) was incubated at room temperature for 30 min with PBAN-R expressed in sf9 cells (*Biochem. Biophys. Res. Commun.* 221, 807-814, 1996), then the non-specifically bound phage was precipitated by centrifugation (10,000 g for 10 min on 4° C.). Next for Step 2, the phage supernatant from Step 1 was transferred into the insect cells expressing the PBAN receptor, and incubated at room temperature for 60 min. Then cells expressing PBAN-R bound to specific phage peptides were precipitated by centrifugation (10,000 g for 10 min 4° C.). For Step 3, the supernatant was decanted to collect the cell pellet, then re-suspended in 50 mM Glycine-HCl (pH, 2.2) and incubated at room temperature for 10 min with shaking. 1M Tris-HCl (pH 9.0) was add to neutralize the solution. Next for Step 4, 20 mL of an *E coli* culture (available from New England Biolabs, Inc.) containing 20 µg/ml Tetracycline was transferred and incubated at 37° C. for 4.5 hrs with vigorous shaking. Next for Step 5, after 4.5 hrs of incubation, the culture was centrifuged at 10,000 g for 10 min at 4° C., then the supernatant was collected and transferred to a fresh tube. Next for Step 6, 20% PEG solution containing 2.5 M NaCl was added to the supernatant, mixed well, and then incubated on ice for 2 hours. Next, for Step 7, the solution was centrifuged at 10,000 g for 20 min at 4° C., and the collected pellet was resuspended in the phosphate saline buffer with 15% glycerol for the next round of screening. Step 7 was repeated 3-4 times. Next for Step 8, after the third or fourth round, 20 or more phage colonies were selected and cultured in *E. coli* to amplify phages. The purified phage DNAs from the culture were sequenced (by ICBR at the University of Florida) to identify nucleotide sequences encoding proteins. A pictorial representation of the procedure is provided in FIG. 1.

Table 1 discloses a group of screened peptides isolated from the libraries described herein after three to four rounds of selection. The listed heptapeptides are loop-constrained by a pair of flanking cysteine (C) residues. It is contemplated that the screened peptides disclosed in Table 1 would be effective in controlling insects.

TABLE 1

Screened library peptides with flanking cysteine residues.

| Phage sequence (CXXXXXXXC) | Abundance of phage clones | Phage sequence (CXXXXXXXC) | Abundance of phage clones |
|---|---|---|---|
| QKIGSHF (SEQ ID NO: 2) | 11 | QSINGHF (SEQ ID NO: 8) | 2 |
| LKIGSHF (SEQ ID NO: 3) | 7 | VKQGTHF (SEQ ID NO: 9) | 2 |
| IQQGSHF (SEQ ID NO: 4) | 3 | IVQGSHF (SEQ ID NO: 10) | 2 |
| ERVGSHF (SEQ ID NO: 5) | 3 | MARYMSA (SEQ ID NO: 11) | 2 |
| VKLGSHF (SEQ ID NO: 6) | 2 | RGATPMS (SEQ ID NO: 12) | 2 |
| IVQGSHF (SEQ ID NO: 7) | | | |

Table 2 discloses an additional group of screened peptides isolated from the libraries described herein after three to four rounds of selection. The listed heptapeptides are loop-constrained by a pair of flanking cysteine (C) residues. It is contemplated that the screened peptides disclosed in Table 2 would also be effective in controlling insects.

TABLE 2

Additional Screened library peptides with flanking cysteine residues.

| Phage sequence (CXXXXXXXC) | Abundance of phage clones | Phage sequence (CXXXXXXXC) | Abundance of phage clones |
|---|---|---|---|
| TXVGSHF (SEQ ID NO: 15) | 1 | IKIGSHY (SEQ ID NO: 26) | 1 |
| IHIGSHF (SEQ ID NO: 16) | 1 | QRIGLHY (SEQ ID NO: 27) | 1 |
| TQIGTHF (SEQ ID NO: 17) | 1 | VSRTSHL (SEQ ID NO: 28) | 1 |
| IQIGTHF (SEQ ID NO: 18) | 1 | LPWQIHN (SEQ ID NO: 29) | 1 |
| QSIGTHF (SEQ ID NO: 19) | 1 | LPMTKHV (SEQ ID NO: 30) | 1 |
| ERVGTHF (SEQ ID NO: 20) | 1 | TNANHYF (SEQ ID NO: 31) | 1 |
| HSRVSGT (SEQ ID NO: 21) | 1 | QQTKNYY (SEQ ID NO: 32) | 1 |
| IHXGTHF (SEQ ID NO: 22) | 1 | TNGDSAR (SEQ ID NO: 33) | 1 |
| YSSPSHF (SEQ ID NO: 23) | 1 | SQLPWYS (SEQ ID NO: 34) | 1 |
| ERVGTHY (SEQ ID NO: 24) | 1 | NTGGSMA (SEQ ID NO: 35) | 1 |
| IKVGPHY (SEQ ID NO: 25) | 1 | NTGSPYE (SEQ ID NO: 36) | 1 |

Peptides identified herein are injected into the hemocoel of *Solenopsis invicta* workers using a Nanoliter 2000™ System (World Precision Instruments) with pulled borosilicate needles.

It is contemplated that peptides identified herein would be dissolved in 10% sucrose solution, or an aqueous 10% sucrose solution (wt./vol.) and fed ad libitum for a period of 14 days via a capillary tube to *Solenopsis invicta* workers.

Example 1: Bioassay of SEQ. ID. NO: 2 SEQ ID NO: 2

To determine the negative impact these peptides may have against fire ants, synthesis of potential candidates of small peptides with Cysteine-Cysteine S-S bond at the N- and C-terminal ends of SEQ ID NO: 2 and SEQ ID NO: 14. Synthesis of the peptides is described above. These peptides were dissolved in an insect saline (composition in mM: NaCl 126, KCl 5.4, NaH2PO4 0.17 and KH2PO4 0.22, pH 7.4) or the saline only control were injected into fire ant workers and phenotypic effects monitored.

Figure 2:
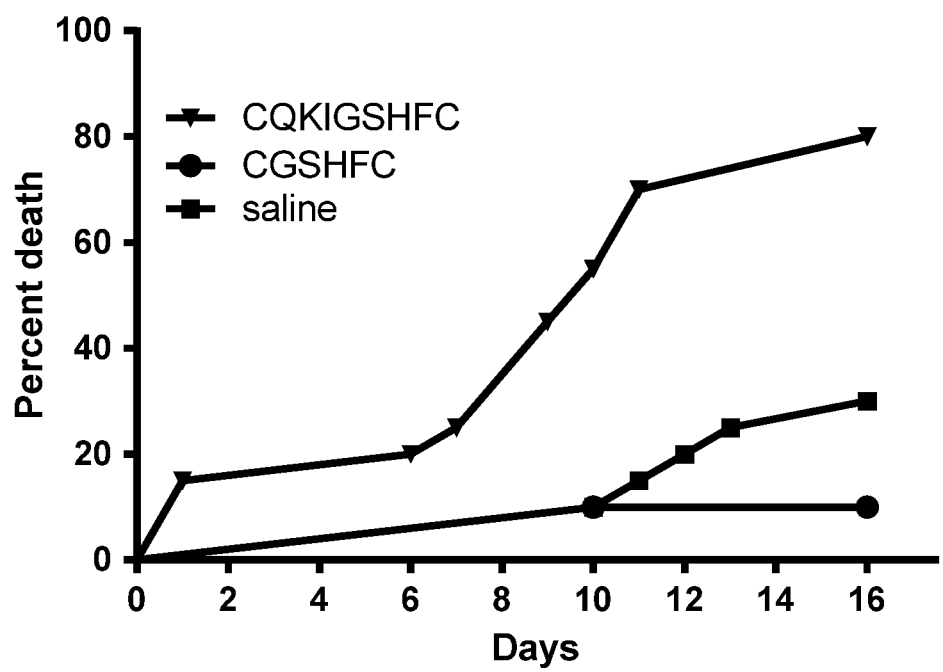
FIG. 2 is a graph depicting mortality of worker *Solenopsis invicta* injected with disclosed peptides.
Figure 3:
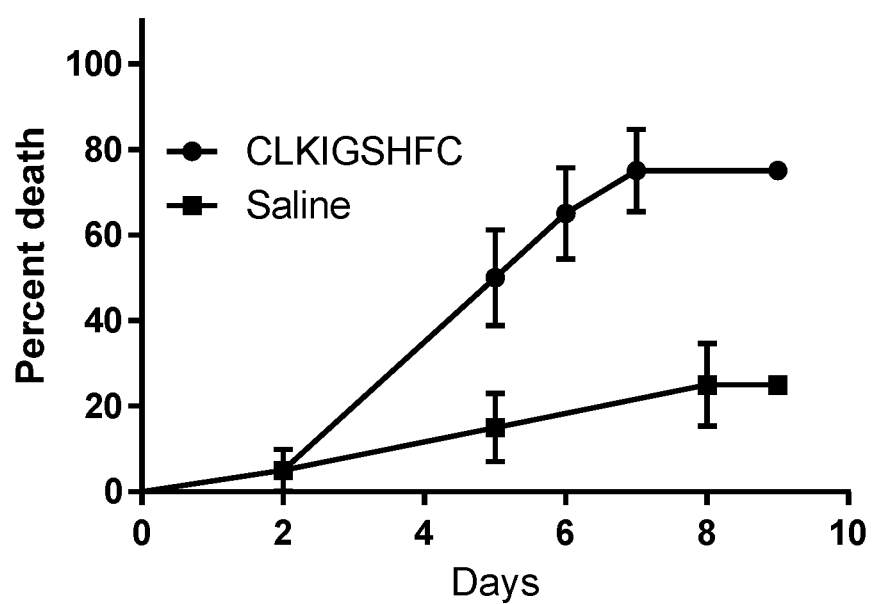
FIG. 3 is a graph depicting mortality of worker *Solenopsis invicta* injected with disclosed peptides.
Figure 4:
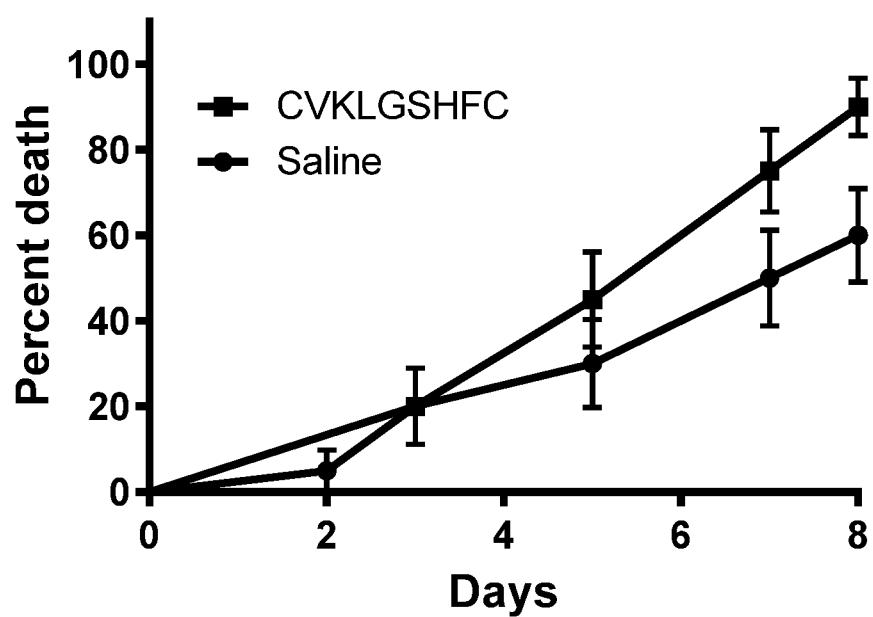
FIG. 4 is a graph depicting mortality of worker *Solenopsis invicta* injected with disclosed peptides.
Figure 5:
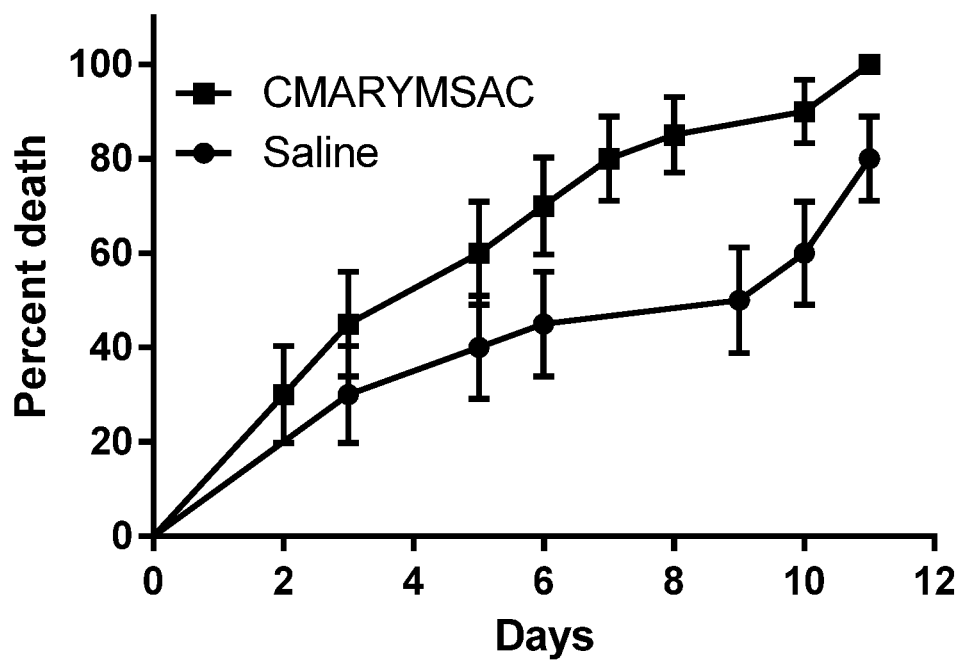
FIG. 5 is a graph depicting mortality of worker *Solenopsis invicta* injected with disclosed peptides.
Figure 6:
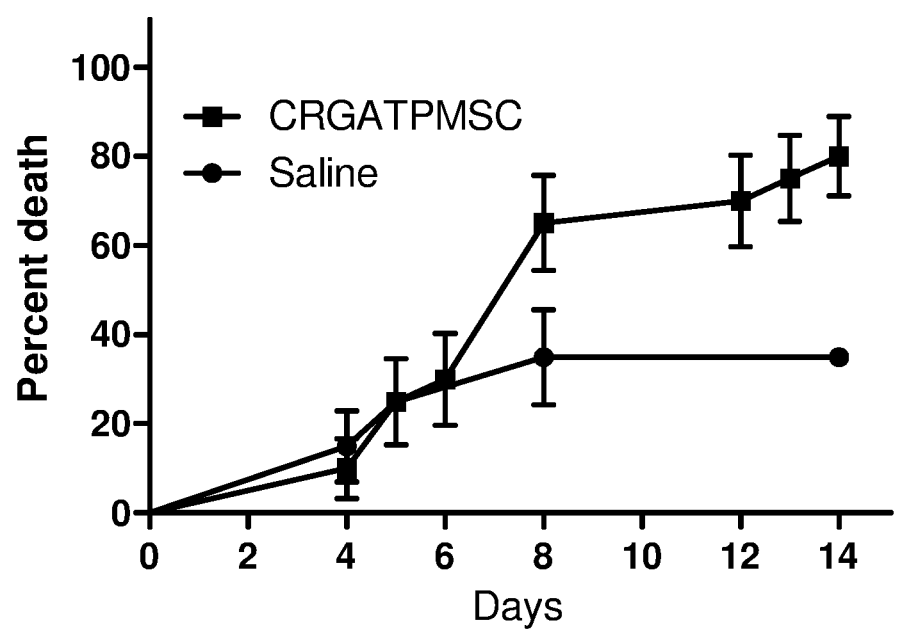
FIG. 6 is a graph depicting mortality of worker *Solenopsis invicta* injected with disclosed peptides.

One of these peptides, CQKIGSHFC (SEQ ID NO: 2) showed a significant ($p<0.0001$) increase in adult mortality compared to the saline control (FIG. 2). The short sequence CGSHFC (SEQ ID NO: 14) was also injected, but it did not affect adult mortality. Therefore, the N-terminal sequence (QKI) is important for binding with the fire ant PBAN-R (acting as an antagonist). This illustrates how the selection results can then be used to understand the importance of certain structural features in order to improve activity or change the mode of action.

Example 2: Bioassay of SEQ ID NO: 3, SEQ ID NO: 6-SEQ ID NO: 11 and SEQ ID NO: 12

To determine the negative impact these peptides may have against fire ants, synthesis of potential candidates of small peptides with Cysteine-Cysteine S-S bond at the N- and C-terminal ends of SEQ ID NO:2-SEQ ID NO:14. Synthesis of the peptides is described above. These peptides were dissolved in an insect saline (composition in mM: NaCl 126, KCl 5.4, NaH2PO4 0.17 and KH2PO4 0.22, pH 7.4) or the saline only control were injected into fire ant workers and phenotypic effects monitored.

In addition to the results shown for the peptide of SEQ ID NO: 2, some of these peptides, CLKIGSHFC (SEQ ID NO: 3, P<0.0012), CVKLGSHFC (SEQ ID NO: 4, P<0.06), CMARYMSAC (SEQ ID NO: 11, P<0.0066), CRGATPMSC (SEQ ID NO: 12, P<0.0180) showed a significant increase in adult mortality compared to the saline control (FIGS. 3-6). The short sequence CGSHFC (SEQ ID NO: 14) was also injected, but it did not affect adult mortality (FIG. 2). Therefore, the N-terminal sequences (QKI and LKI) are important for binding with the fire ant PBAN-R (acting as an antagonist). Also two peptides, MARYMSA (SEQ ID NO: 11, without the terminal cysteine residues) and RGATPMS (SEQ ID NO: 12, without the terminal cysteine residues), that are not similar and unique, also act as an antagonist and/or agonist to PBAN-R. This illustrates how the selection results can then be used to understand the importance of certain structural features in order to improve activity or change the mode of action.

While the invention has been described with reference to details of the illustrated embodiment, these details are not intended to limit the scope of the invention as defined in the appended claims. The embodiment of the invention in which exclusive property or privilege is claimed is defined as follows:

The invention claimed is:

1. An insecticide composition for controlling an insect, the composition comprising an effective amount of peptide having SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, or a combination thereof.

2. The composition of claim 1, further compromising an insecticide carrier.

3. The composition of claim 2, wherein the carrier is saline.

4. The composition of claim 1, wherein the peptide has SEQ ID NO: 3, SEQ ID NO: 6, or a combination thereof.

5. The composition of claim 1, further comprising one or more suitable carriers, diluents, adjuvants, preservatives, dispersants, solvents, or emulsifying agents.

6. A spray composition for controlling an insect, comprising: (a) an effective amount of the composition of claim 1; and (b) a propellant.

7. A bait composition for controlling an insect, comprising:
(a) an effective amount of the composition of claim 1,
(b) one or more food materials; and
(c) optionally a phagostimulant.

8. A composition comprising an isolated synthetic peptide consisting of nine amino acids, wherein the peptide has SEQ ID NO: 1, and a carrier.

9. The composition of claim 8, further comprising an insecticide carrier.

10. The composition of claim 8, further comprising one or more suitable carriers, diluents, adjuvants, preservatives, dispersants, solvents, or emulsifying agents.

11. The composition of claim 8, further comprising a propellant.

12. The composition of claim 8, further comprising one or more foodstuffs and optionally an insect phagostimulant.

13. A method for controlling an insect comprising contacting an insect or its environment with a biologically effective amount of a compound of claim 1, wherein the mortality of said insect increases.

14. The method of claim 13, wherein the insect is a *Solenopsis* spp.

15. The method of claim 14, wherein the insect is the *Solenopsis invicta*.

* * * * *

SEQUENCE LISTING

```
<160> NUMBER OF SEQ ID NOS: 36

<210> SEQ ID NO 1
<211> LENGTH: 9
<212> TYPE: PRT
<213> ORGANISM: ARTIFICIAL SEQUENCE
<220> FEATURE:
<223> OTHER INFORMATION: Peptide motif
<220> FEATURE:
<221> NAME/KEY: misc_feature
<222> LOCATION: (2)..(5)
<223> OTHER INFORMATION: Xaa can be any naturally occurring amino acid

<400> SEQUENCE: 1

Cys Xaa Xaa Xaa Xaa Ser His Phe Cys
1               5

<210> SEQ ID NO 2
<211> LENGTH: 9
<212> TYPE: PRT
<213> ORGANISM: ARTIFICIAL SEQUENCE
<220> FEATURE:
<223> OTHER INFORMATION: Synthetically generated peptide

<400> SEQUENCE: 2

Cys Gln Lys Ile Gly Ser His Phe Cys
1               5

<210> SEQ ID NO 3
<211> LENGTH: 9
<212> TYPE: PRT
<213> ORGANISM: ARTIFICIAL SEQUENCE
<220> FEATURE:
<223> OTHER INFORMATION: Synthetically generated peptide

<400> SEQUENCE: 3

Cys Leu Lys Ile Gly Ser His Phe Cys
1               5

<210> SEQ ID NO 4
<211> LENGTH: 9
<212> TYPE: PRT
<213> ORGANISM: ARTIFICIAL SEQUENCE
<220> FEATURE:
<223> OTHER INFORMATION: Synthetically generated peptide

<400> SEQUENCE: 4

Cys Ile Gln Gln Gly Ser His Phe Cys
```

```
1               5
```

```
<210> SEQ ID NO 5
<211> LENGTH: 9
<212> TYPE: PRT
<213> ORGANISM: ARTIFICIAL SEQUENCE
<220> FEATURE:
<223> OTHER INFORMATION: Synthetically generated peptide

<400> SEQUENCE: 5

Cys Glu Arg Val Gly Ser His Phe Cys
1               5

<210> SEQ ID NO 6
<211> LENGTH: 9
<212> TYPE: PRT
<213> ORGANISM: ARTIFICIAL SEQUENCE
<220> FEATURE:
<223> OTHER INFORMATION: Synthetically generated peptide

<400> SEQUENCE: 6

Cys Val Lys Leu Gly Ser His Phe Cys
1               5

<210> SEQ ID NO 7
<211> LENGTH: 9
<212> TYPE: PRT
<213> ORGANISM: ARTIFICIAL SEQUENCE
<220> FEATURE:
<223> OTHER INFORMATION: Synthetically generated peptide

<400> SEQUENCE: 7

Cys Ile Val Gln Gly Ser His Phe Cys
1               5

<210> SEQ ID NO 8
<211> LENGTH: 9
<212> TYPE: PRT
<213> ORGANISM: ARTIFICIAL SEQUENCE
<220> FEATURE:
<223> OTHER INFORMATION: Synthetically generated peptide

<400> SEQUENCE: 8

Cys Gln Ser Ile Asn Gly His Phe Cys
1               5

<210> SEQ ID NO 9
<211> LENGTH: 9
<212> TYPE: PRT
<213> ORGANISM: ARTIFICIAL SEQUENCE
<220> FEATURE:
<223> OTHER INFORMATION: Synthetically generated peptide

<400> SEQUENCE: 9

Cys Val Lys Gln Gly Thr His Phe Cys
1               5

<210> SEQ ID NO 10
<211> LENGTH: 9
<212> TYPE: PRT
<213> ORGANISM: ARTIFICIAL SEQUENCE
<220> FEATURE:
<223> OTHER INFORMATION: Synthetically generated peptide

<400> SEQUENCE: 10

Cys Ile Val Gln Gly Ser His Phe Cys
1               5
```

<210> SEQ ID NO 11
<211> LENGTH: 9
<212> TYPE: PRT
<213> ORGANISM: ARTIFICIAL SEQUENCE
<220> FEATURE:
<223> OTHER INFORMATION: Synthetically generated peptide

<400> SEQUENCE: 11

Cys Met Ala Arg Tyr Met Ser Ala Cys
1               5

<210> SEQ ID NO 12
<211> LENGTH: 9
<212> TYPE: PRT
<213> ORGANISM: ARTIFICIAL SEQUENCE
<220> FEATURE:
<223> OTHER INFORMATION: Synthetically generated peptide

<400> SEQUENCE: 12

Cys Arg Gly Ala Thr Pro Met Ser Cys
1               5

<210> SEQ ID NO 13
<211> LENGTH: 26
<212> TYPE: PRT
<213> ORGANISM: ARTIFICIAL SEQUENCE
<220> FEATURE:
<223> OTHER INFORMATION: PBAN amino acid sequence for Solenopsis invicta

<400> SEQUENCE: 13

Gly Ser Gly Glu Asp Leu Ser Tyr Gly Asp Ala Tyr Glu Val Asp Glu
1               5                   10                  15

Asp Asp His Pro Leu Phe Val Pro Arg Leu
            20                  25

<210> SEQ ID NO 14
<211> LENGTH: 6
<212> TYPE: PRT
<213> ORGANISM: ARTIFICIAL SEQUENCE
<220> FEATURE:
<223> OTHER INFORMATION: Synthetically generated peptide

<400> SEQUENCE: 14

Cys Gly Ser His Phe Cys
1               5

<210> SEQ ID NO 15
<211> LENGTH: 9
<212> TYPE: PRT
<213> ORGANISM: ARTIFICIAL SEQUENCE
<220> FEATURE:
<223> OTHER INFORMATION: Synthetically generated peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 15

Cys Thr Xaa Val Gly Ser His Phe Cys
1               5

<210> SEQ ID NO 16
<211> LENGTH: 9
<212> TYPE: PRT
<213> ORGANISM: ARTIFICIAL SEQUENCE
<220> FEATURE:

```
<223> OTHER INFORMATION: Synthetically generated peptide

<400> SEQUENCE: 16

Cys Ile His Ile Gly Ser His Phe Cys
1               5

<210> SEQ ID NO 17
<211> LENGTH: 9
<212> TYPE: PRT
<213> ORGANISM: ARTIFICIAL SEQUENCE
<220> FEATURE:
<223> OTHER INFORMATION: Synthetically generated peptide

<400> SEQUENCE: 17

Cys Thr Gln Ile Gly Thr His Phe Cys
1               5

<210> SEQ ID NO 18
<211> LENGTH: 9
<212> TYPE: PRT
<213> ORGANISM: ARTIFICIAL SEQUENCE
<220> FEATURE:
<223> OTHER INFORMATION: Synthetically generated peptide

<400> SEQUENCE: 18

Cys Ile Gln Ile Gly Thr His Phe Cys
1               5

<210> SEQ ID NO 19
<211> LENGTH: 9
<212> TYPE: PRT
<213> ORGANISM: ARTIFICIAL SEQUENCE
<220> FEATURE:
<223> OTHER INFORMATION: Synthetically generated peptide

<400> SEQUENCE: 19

Cys Gln Ser Ile Gly Thr His Phe Cys
1               5

<210> SEQ ID NO 20
<211> LENGTH: 9
<212> TYPE: PRT
<213> ORGANISM: ARTIFICIAL SEQUENCE
<220> FEATURE:
<223> OTHER INFORMATION: Synthetically generated peptide

<400> SEQUENCE: 20

Cys Glu Arg Val Gly Thr His Phe Cys
1               5

<210> SEQ ID NO 21
<211> LENGTH: 9
<212> TYPE: PRT
<213> ORGANISM: ARTIFICIAL SEQUENCE
<220> FEATURE:
<223> OTHER INFORMATION: Synthetically generated peptide

<400> SEQUENCE: 21

Cys His Ser Arg Val Ser Gly Thr Cys
1               5

<210> SEQ ID NO 22
<211> LENGTH: 9
<212> TYPE: PRT
<213> ORGANISM: ARTIFICIAL SEQUENCE
<220> FEATURE:
<223> OTHER INFORMATION: Synthetically generated peptide
```

```
<220> FEATURE:
<221> NAME/KEY: misc_feature
<222> LOCATION: (4)..(4)
<223> OTHER INFORMATION: Xaa can be any naturally occurring amino acid

<400> SEQUENCE: 22

Cys Ile His Xaa Gly Thr His Phe Cys
1               5

<210> SEQ ID NO 23
<211> LENGTH: 9
<212> TYPE: PRT
<213> ORGANISM: ARTIFICIAL SEQUENCE
<220> FEATURE:
<223> OTHER INFORMATION: Synthetically generated peptide

<400> SEQUENCE: 23

Cys Tyr Ser Ser Pro Ser His Phe Cys
1               5

<210> SEQ ID NO 24
<211> LENGTH: 9
<212> TYPE: PRT
<213> ORGANISM: ARTIFICIAL SEQUENCE
<220> FEATURE:
<223> OTHER INFORMATION: Synthetically generated peptide

<400> SEQUENCE: 24

Cys Glu Arg Val Gly Thr His Tyr Cys
1               5

<210> SEQ ID NO 25
<211> LENGTH: 9
<212> TYPE: PRT
<213> ORGANISM: ARTIFICIAL SEQUENCE
<220> FEATURE:
<223> OTHER INFORMATION: Synthetically generated peptide

<400> SEQUENCE: 25

Cys Ile Lys Val Gly Pro His Tyr Cys
1               5

<210> SEQ ID NO 26
<211> LENGTH: 9
<212> TYPE: PRT
<213> ORGANISM: ARTIFICIAL SEQUENCE
<220> FEATURE:
<223> OTHER INFORMATION: Synthetically generated peptide

<400> SEQUENCE: 26

Cys Ile Lys Ile Gly Ser His Tyr Cys
1               5

<210> SEQ ID NO 27
<211> LENGTH: 9
<212> TYPE: PRT
<213> ORGANISM: ARTIFICIAL SEQUENCE
<220> FEATURE:
<223> OTHER INFORMATION: Synthetically generated peptide

<400> SEQUENCE: 27

Cys Gln Arg Ile Gly Leu His Tyr Cys
1               5

<210> SEQ ID NO 28
<211> LENGTH: 9
<212> TYPE: PRT
```

```
<213> ORGANISM: ARTIFICIAL SEQUENCE
<220> FEATURE:
<223> OTHER INFORMATION: Synthetically generated peptide

<400> SEQUENCE: 28

Cys Val Ser Arg Thr Ser His Leu Cys
1               5

<210> SEQ ID NO 29
<211> LENGTH: 9
<212> TYPE: PRT
<213> ORGANISM: ARTIFICIAL SEQUENCE
<220> FEATURE:
<223> OTHER INFORMATION: Synthetically generated peptide

<400> SEQUENCE: 29

Cys Leu Pro Trp Gln Ile His Asn Cys
1               5

<210> SEQ ID NO 30
<211> LENGTH: 9
<212> TYPE: PRT
<213> ORGANISM: ARTIFICIAL SEQUENCE
<220> FEATURE:
<223> OTHER INFORMATION: Synthetically generated peptide

<400> SEQUENCE: 30

Cys Leu Pro Met Thr Lys His Val Cys
1               5

<210> SEQ ID NO 31
<211> LENGTH: 9
<212> TYPE: PRT
<213> ORGANISM: ARTIFICIAL SEQUENCE
<220> FEATURE:
<223> OTHER INFORMATION: Synthetically generated peptide

<400> SEQUENCE: 31

Cys Thr Asn Ala Asn His Tyr Phe Cys
1               5

<210> SEQ ID NO 32
<211> LENGTH: 9
<212> TYPE: PRT
<213> ORGANISM: ARTIFICIAL SEQUENCE
<220> FEATURE:
<223> OTHER INFORMATION: Synthetically generated peptide

<400> SEQUENCE: 32

Cys Gln Gln Thr Lys Asn Tyr Tyr Cys
1               5

<210> SEQ ID NO 33
<211> LENGTH: 9
<212> TYPE: PRT
<213> ORGANISM: ARTIFICIAL SEQUENCE
<220> FEATURE:
<223> OTHER INFORMATION: Synthetically generated peptide

<400> SEQUENCE: 33

Cys Thr Asn Gly Asp Ser Ala Arg Cys
1               5

<210> SEQ ID NO 34
<211> LENGTH: 9
<212> TYPE: PRT
<213> ORGANISM: ARTIFICIAL SEQUENCE
```

```
<220> FEATURE:
<223> OTHER INFORMATION: Synthetically generated peptide

<400> SEQUENCE: 34

Cys Ser Gln Leu Pro Trp Tyr Ser Cys
1               5

<210> SEQ ID NO 35
<211> LENGTH: 9
<212> TYPE: PRT
<213> ORGANISM: ARTIFICIAL SEQUENCE
<220> FEATURE:
<223> OTHER INFORMATION: Synthetically generated peptide

<400> SEQUENCE: 35

Cys Asn Thr Gly Gly Ser Met Ala Cys
1               5

<210> SEQ ID NO 36
<211> LENGTH: 9
<212> TYPE: PRT
<213> ORGANISM: ARTIFICIAL SEQUENCE
<220> FEATURE:
<223> OTHER INFORMATION: Synthetically generated peptide

<400> SEQUENCE: 36

Cys Asn Thr Gly Ser Pro Tyr Glu Cys
1               5
```